(12) United States Patent
Hayashizaki et al.

(10) Patent No.: US 6,783,650 B2
(45) Date of Patent: Aug. 31, 2004

(54) CAPILLARY ELECTROPHORETIC APPARATUS

(75) Inventors: Yoshihide Hayashizaki, Ibaraki (JP); Shin Nakamura, Kyoto (JP)

(73) Assignees: The Institute of Physical & Chemical Research, Saitama (JP); Shimadzu Corporation, Kyoto (JP)

( * ) Notice: Subject to any disclaimer, the term of this patent is extended or adjusted under 35 U.S.C. 154(b) by 186 days.

(21) Appl. No.: 10/126,661

(22) Filed: Apr. 22, 2002

(65) Prior Publication Data

US 2002/0117398 A1 Aug. 29, 2002

Related U.S. Application Data

(62) Division of application No. 09/443,719, filed on Nov. 19, 1999, now Pat. No. 6,461,492.

(30) Foreign Application Priority Data

Nov. 30, 1998 (JP) .......................................... 10-338897
Nov. 30, 1998 (JP) .......................................... 10-338899
May 12, 1999 (JP) .......................................... 11-130814

(51) Int. Cl.[7] .................. C02F 1/40; C02F 11/00; C25B 11/00; C25B 13/00; C25B 9/00
(52) U.S. Cl. ..................... 204/603; 204/450; 204/601
(58) Field of Search ............................... 204/601, 450

(56) References Cited

U.S. PATENT DOCUMENTS

| | | | |
|---|---|---|---|
| 4,929,329 A | | 5/1990 | Danby et al. |
| 4,941,932 A | * | 7/1990 | John .......................... 156/48 |
| 5,141,314 A | | 8/1992 | Belmore et al. |
| 5,439,578 A | | 8/1995 | Dovichi et al. |
| 5,516,409 A | | 5/1996 | Kambara |
| 5,560,811 A | | 10/1996 | Briggs et al. |
| 5,710,850 A | * | 1/1998 | Watanabe et al. .............. 385/71 |
| 5,730,850 A | * | 3/1998 | Kambara et al. ............ 204/603 |
| 5,832,162 A | * | 11/1998 | Sarbell .......................... 385/99 |
| 5,885,430 A | | 3/1999 | Kernan et al. |
| 5,916,428 A | | 6/1999 | Kane et al. |
| 6,054,032 A | * | 4/2000 | Haddad et al. ............. 204/451 |
| 6,063,251 A | * | 5/2000 | Kane et al. ................. 204/601 |
| 6,174,352 B1 | * | 1/2001 | Semerdjian et al. ............. 96/8 |
| 6,461,492 B1 | * | 10/2002 | Hayashizaki et al. ....... 204/603 |

FOREIGN PATENT DOCUMENTS

| | | |
|---|---|---|
| DE | 4230354 A1 | 3/1993 |
| EP | 0441463 A1 | 8/1991 |
| EP | 0479137 A2 | 4/1992 |
| WO | WO 96/36872 | 11/1996 |
| WO | WO 98/14773 | 4/1998 |
| WO | WO 98/23945 | 6/1998 |
| WO | WO 98/43072 | 10/1998 |

OTHER PUBLICATIONS http://stwi.weizmann.ac.il/Lasers/laserweb/Ch-1/C1s1p1.htm.
www.biotium.com/prodindex/miscell/80101.htm.
http://www.omic.ogi.edu/spectra/PhotochemCAD/html/sulforhodamine101.html.
www.calvin.edu/~muym/dyetable.htm.
http://library.thinkquest.org/16468/apndx5.htm.
"Highly Sensitive Detection Using Laser Two-Photon Excited Fluorescence in Capillary Electrophoresis," Journal of Chromatography A, Elsevier Science, vol. 765, No. 2 (1997), pp. 315-319.

* cited by examiner

Primary Examiner—Mark L. Bell
Assistant Examiner—Jennine Brown
(74) Attorney, Agent, or Firm—Rader Fishman & Grauer

(57) ABSTRACT

A capillary cassette is made up of two separated holders, an array of capillaries and a tube. The capillaries that make up the array are inserted into the first holder, extend through second holder having a detection window and then the capillary array is aligned and then bundled and inserted into a heat shrinkable tube which covers positions to which filler is applied, the tube is heated and shrunk to bundle them in an airtight manner and inserted into a mounting member.

4 Claims, 14 Drawing Sheets

Fig. 3
(A)
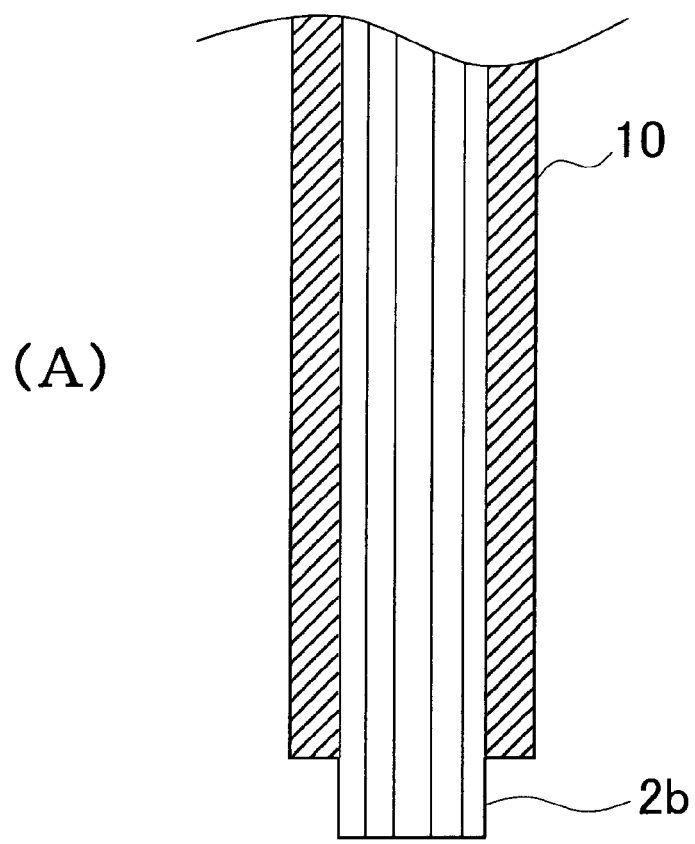
(B)
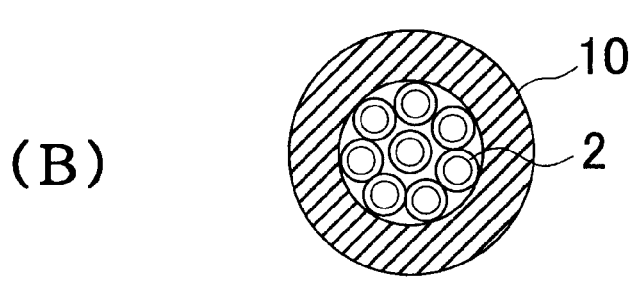

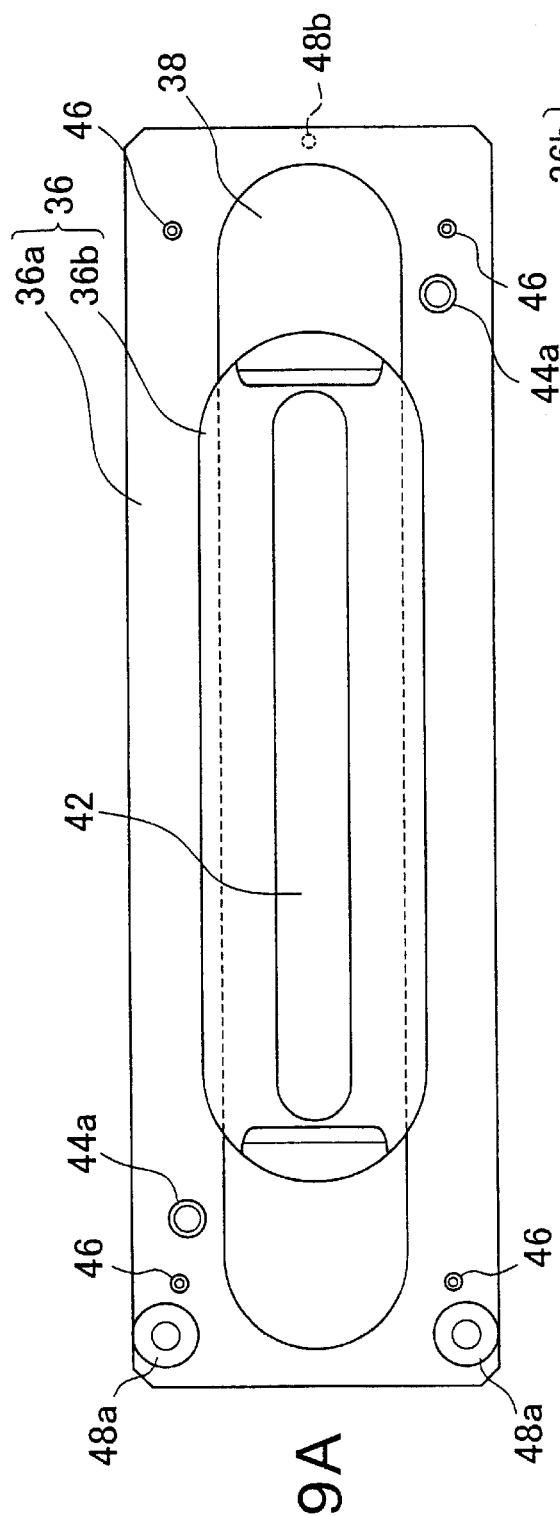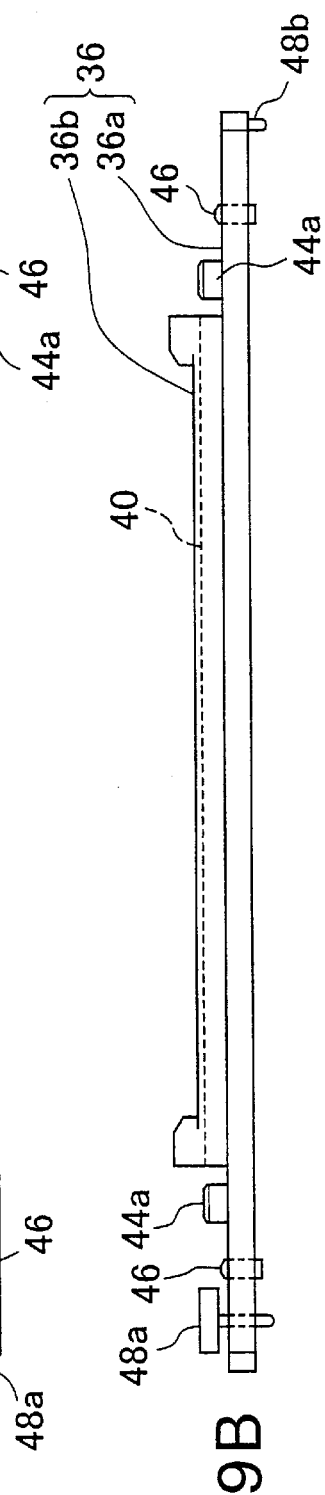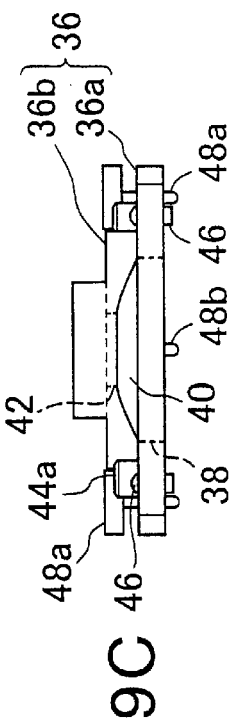

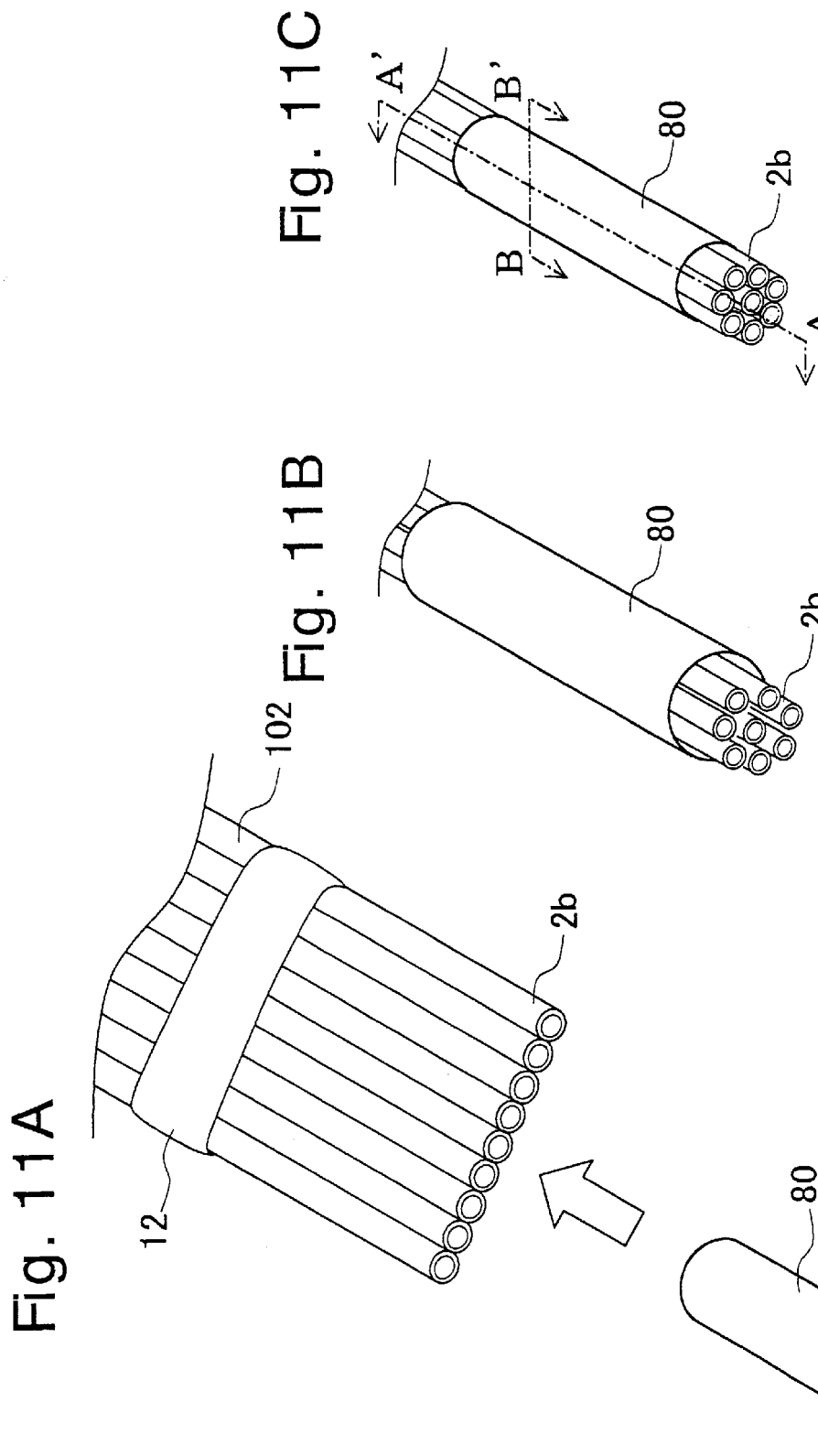

CAPILLARY ELECTROPHORETIC APPARATUS

This is a divisional of application Ser. No. 09/443,719, filed Nov. 19, 1999, now U.S. Pat. No. 6,461,492.

BACKGROUND OF THE INVENTION

1. Field of the Invention

The present invention relates to a capillary electrophoretic apparatus for separating and analyzing a biopolymer such as protein or nucleic acid.

Such a capillary electrophoretic apparatus is applied to sequence determination for DNA. The capillary electrophoretic apparatus for DNA sequence determination electrophoreses a DNA fragment sample prepared by labeling a primer or a terminator with a fluorochrome and detects fluorescence from the DNA fragment sample during electrophoresis for determining the base sequence.

2. Description of the Prior Art

A DNA sequencer having high sensitivity, a high speed and high throughput is necessary for sequence determination for DNA such as a human genome having long base sequence. As an example, capillary electrophoresis employing a capillary column charged with a gel in place of slab gel electrophoresis employing a flat plate type slab gel is proposed. With such a capillary column, a sample can not only be readily handled or injected but also electrophoresed at a high speed and detected in high sensitivity as compared with the slab gel. If a high voltage is applied to the slab gel, a band is spread or a temperature gradient is caused due to influence by Joulean heat. However, the capillary column hardly causes such a problem and can perform detection in high sensitivity with small band spreading even if performing high-speed electrophoresis with application of a high voltage.

A multi-capillary electrophoretic apparatus prepared by arranging a plurality of capillary columns is also proposed.

An automatic DNA sequencer utilizes a fluorochrome for identifying the four types of bases forming DNA. A Rhodamine derivative such as R6G, R-110 or ROX or a fluorescein derivative such as FAM is utilized as the fluorochrome. An argon ion laser unit having dominant wavelengths of 488.0 nm and 514.5 nm is utilized as a laser beam source.

However, both of the wavelengths of 488.0 nm and 514.5 nm are separate from the absorption maximum wavelengths of the fluorescein derivatives and the Rhodamine derivatives. While fluorescein derivatives having an absorption maximum wavelength of 493.5 nm are not much reduced in efficiency, the Rhodamine derivatives, which are excited at 514.5 nm although its absorption maximum wavelength is 550 nm, has inferior efficiency.

In order to solve this problem, there has been made an attempt (referred to as an energy transfer method) of introducing both of the fluorescein derivative and the Rhodamine derivative into the same molecule when using the Rhodamine derivative as a label thereby improving the efficiency of the Rhodamine derivative through the principle of energy transfer.

The energy transfer method is superior to general methods, but yet has the following problems:

1. It is technically difficult to introduce a plurality of fluorochromes into the same molecule, and the cost is increased following this difficulty.
2. Extreme influence is exerted by Raman scattering since the excitation wavelength is in the visible region. When excited at 488 nm, a Raman scattering line of water around 516 nm forms background noise of a channel detecting the fluorescein derivative having a fluorescence maximum at 510 nm to reduce an S-N (signal-to-noise) ratio.
3. Influence is exerted by Rayleigh scattering to readily reduce the S-N ratio.

Considering a multi-capillary electrophoretic apparatus in which a plurality of capillary columns are so arranged that a plurality of samples are injected into the capillary columns and simultaneously electrophoresed in all capillary columns, one ends of the plurality of capillary columns defining a sample injection side are two-dimensionally arranged and fixed by a sample injection side holder while the other ends defining a detection side are aligned with each other on a plane and fixed by a detection side holder for forming a capillary array. The detection side holder is provided with a slot along the arrangement of the capillary columns, and parts of the capillary columns exposed through the slot define a part to be detected. When separating and detecting a sample containing a DNA fragment labeled in four types with a fluorescent material, excitation light is applied to the part to be detected for detecting fluorescence generated from sample components electrophoresed to the part to be detected thereby identifying the sample components.

The prior art employs an epi-optical system comprising a condenser lens condensing and projecting excitation light onto each capillary column on the part to be detected and receiving the fluorescence generated from the sample electrophoresed in the capillary column as an objective lens for projecting the excitation light and receiving the fluorescence through the same lens as an excitation-light receiving optical system. The objective lens is scanned along a straight line parallel to the plane of arrangement of the capillary columns on the part to be detected and perpendicular to the electrophoresis direction, thereby detecting the fluorescence as to all capillary columns.

In such an optical system, the objective lens is preferably arranged in proximity to the part to be detected for collecting the maximum amount of fluorescence in consideration of detection sensitivity. Therefore, the condenser lens having a short focal length is employed as the objective lens.

When employing the condenser lens having a short focal length as the objective lens, the amount of collected fluorescence is reduced to reduce the detection sensitivity if the position of the part to be detected of the capillary array slightly deviates in the direction of application of the excitation light. Therefore, high working accuracy is required when preparing the detection side holder and fixing the capillary columns to the detection side holder.

In the multi-capillary electrophoretic apparatus, the capillary columns are fixed to cassette holders on a sample introduction side and the detection side. The cassette holders two-dimensionally arrange the capillary columns on the sample introduction side and planarly align the same with each other on the detection side.

When charging each capillary column with a polymer, one end of the capillary column is stuck into and fixed to an elastic member such as a rubber stopper or fixed to a dedicated holder for polymer charging with an adhesive for filling up a clearance. The polymer is charged into the capillary column by fixing the elastic member or the dedicated holder to a vessel storing the polymer so that the end of the capillary column is dipped in the polymer, sealing the vessel and pressurizing the vessel with a pump for press-filling the polymer into the capillary column, or by connecting the elastic member or the dedicated holder to a pump, dipping another end of the capillary column into the polymer and decompressing the capillary column with the pump for inhaling the polymer into the capillary column.

When charging the polymer into the capillary column by press-filling or inhaling in the method of sticking and fixing the capillary column into and to the elastic member, pressure resistance of the elastic member may be so insufficient that the polymer cannot be smoothly charged into the capillary column. On the other hand, in the method of fixing the capillary column to the dedicated holder for polymer charging with an adhesive, it may be impossible to smoothly charge the polymer into the capillary column due to insufficient supply of the adhesive, to result in an inferior manufacturing yield.

SUMMARY OF THE INVENTION

A first objective of the present invention is to perform efficient detection in a capillary electrophoretic apparatus.

A second objective of the present invention is to provide a capillary cassette capable of reliably charging all capillary columns with polymers with a high yield in a multi-capillary electrophoretic apparatus.

A first aspect of the present invention for performing efficient detection comprises detection means exciting a fluorochrome bonded to a sample component as a label for making the same fluoresce and detecting the generated fluorescence without influence by Raman scattering or Rayleigh scattering. In a capillary electrophoretic apparatus according to the present invention, the detection means applies excitation light having a wavelength longer than the fluorescent wavelength of the fluorochrome, excites the fluorochrome by multiphoton absorption and detects fluorescence generated from the fluorochrome. In other words, this aspect utilizes a multiphoton absorption method of applying light (the excitation light having a longer wavelength than the fluorescent wavelength of the fluorochrome) having energy of one photon smaller than excitation energy for the fluorochrome to the sample bonded with the fluorochrome and making the fluorochrome absorb multiphotons thereby exciting the fluorochrome and making the same fluoresce.

In the multiphoton absorption method, both a fluorescein derivative and a Rhodamine derivative can be excited with a common laser wavelength. Therefore, it is not necessary to introduce a plurality of fluorochromes into the same molecule.

The excitation wavelength used in the multiphoton absorption method may be set in a range from 400 nm to 2 $\mu$m, and preferably is set in the near infrared region of at least 600 nm. With the excitation wavelength of at least 600 nm, most of the Raman scattering line outgoing from the wavelength is Stokes Raman scattered light having a wavelength of at least 600 nm. Therefore, the Raman scattering light does not form background noise in detection of fluorescence from fluorescein or Rhodamine.

Furthermore, the intensity of Rayleigh scattering is in inverse proportion to the sixth power of the wavelength, and hence the excitation light of a longer wavelength region exceeding 600 nm utilized in the multiphoton absorption method is superior to an argon laser beam for suppressing Rayleigh scattering.

Thus, the fluorescence from the fluorochrome can be detected in a high S-N ratio while suppressing influence by Raman scattering and Rayleigh scattering by comprising the detection means employing the multiphoton absorption method, applying the light of a wavelength longer than the fluorescent wavelength of the fluorochrome to the fluorochrome for exciting the same and detecting the fluorescence thereof.

A second aspect of the present invention for performing efficient detection is to relieve requirement for working accuracy at the time of preparing a detection side holder and fixation of capillary columns to the detection holder, fix the position of a part to be detected of a capillary array to the apparatus with excellent reproducibility, and suppress reduction of detection sensitivity. in a multi-capillary electrophoretic apparatus The multi-capillary electrophoretic apparatus to which this aspect is applied comprises a capillary array in which a plurality of capillary columns are so arranged that one ends defining a sample injection side are fixed by a sample injection side holder, the other ends defining a detection side are aligned with each other on a plane and fixed by a detection side holder and a part to be detected is provided on the position of the detection side holder, a multi-capillary array electrophoresis part to which the sample injection side holder and the detection side holder are fixed so that samples are injected into the capillary columns, the ends on the sample injection side are dipped into a buffer solution, the ends on the detection side are dipped into another buffer solution and an electrophoresis voltage is applied through both buffer solutions for performing electrophoresis in all capillary columns, and a detection part applying light to the part to be detected of the capillary array and detecting light affected by interaction with the samples. According to this aspect, the multi-capillary array electrophoresis part includes a detection side holder fixing part fixing the detection side holder and a parallelism adjusting mechanism adjusting the parallelism between the detection part and the part to be detected.

Detection can be performed in constant sensitivity regardless of the position of the part to be detected by adjusting the parallelism between the detection part and the part to be detected by the parallelism adjusting mechanism.

The detection system of the detection part may be either a scanning system of sequentially detecting the capillary columns one by one on the part to be detected or an image system of collectively capturing the capillary columns on the part to be detected as an image.

The detection part in the scanning system comprises an epi-optical system condensing and projecting light onto one of the capillary columns on the part to be detected while receiving light affected by interaction with the samples and a scanning mechanism reciprocally moving the epi-optical system along a straight line parallel to the plane of arrangement on the part to be detected of the capillary array and perpendicular to the electrophoresis direction, and the parallelism adjusting mechanism adjusts the parallelism between a scanning axis of the epi-optical system and the part to be detected in this case.

In the parallelism adjustment, the scanning system fixes the detection side holder to the detection side holder fixing part, thereafter drives the scanning mechanism to reciprocate the epi-optical system in the direction perpendicular to the electrophoresis direction, and adjusts the parallelism between the scanning axis of the epi-optical system and the part to be detected by the parallelism adjusting mechanism on the basis of a current detection signal of the detection part.

The image system can be provided with an imaging optical system and a line sensor described in, for example, U.S. Pat. No. 5,534,703. In this case, the parallelism adjusting mechanism may adjust an optical axis of the imaging optical system.

A mode of the parallelism adjusting mechanism is preferably a gate adjusting mechanism adjusting a mounting angle of the detection side holder fixing part by rotation of a screw. Consequently, the parallelism between the scanning axis of the epi-optical system and the part to be detected can be adjusted in a simple structure through a simple operation.

Another mode of the parallelism adjusting mechanism preferably comprises an actuator automatically adjusting a gate angle of the detection side holder fixing part in correspondence to the detection signal at the time of scanning the epi-optical system. Consequently, a burden on an operator can be reduced.

Furthermore, the detection part preferably comprises an epi-optical system condensing and projecting light onto each capillary column on the part to be detected and receiving light affected by interaction with the samples, and a scanning mechanism reciprocally moving the epi-optical system along a straight line perpendicular to the electrophoresis direction while automatically adjusting the distance between the part to be detected and the epi-optical system in correspondence to a detection signal at the time scanning the same along the straight line. Consequently, the distance between the part to be detected and the epi-optical system can be rendered suitable without providing a parallelism adjusting mechanism.

The detection side holder fixing part preferably comprises a detection position member arranged between the part to be detected and the epi-optical system, having an opening on a position corresponding to the part to be detected and having a plane in contact with one surface of the part to be detected and a detected part pressing member having a plane pressing the part to be detected against the detection position member from a side opposite from the detection position member. Consequently, the plurality of capillary columns of the part to be detected can be fixed onto the plane of the detection position member with exceptional reproducibility.

The inventive multi-capillary electrophoretic apparatus according to this aspect fixes the part to be detected of the capillary array onto a plane of a movable plate by the detected part pressing member and thereafter adjusts a gate angle of the movable plate by a gate adjusting mechanism so that the parallelism between the part to be detected and the scanning axis of the epi-optical system can be adjusted, whereby requirement for working accuracy in preparation of the detection side holder and fixation of the capillary columns to the detection side holder can be relaxed, the position of the part to be detected can be fixed to the apparatus with excellent reproducibility, and reduction of detection sensitivity can be suppressed.

A capillary cassette according to the present invention capable of reliably charging all capillary columns with polymers in an excellent yield is a capillary cassette in which a plurality of capillary columns used in a multi-capillary electrophoretic apparatus are bundled so that first ends thereof are cylindrically bundled by a sleeve and clearances between the sleeve and the capillary columns and between the capillary columns are sealed with a filler.

The one ends of the capillary columns cylindrically bundled by the sleeve have a cylindrical outer shape and hence can be readily mounted on a polymer charger in an airtight manner, whereby the capillary columns can be readily charged with the polymers through a high pressure.

The sleeve is preferably prepared by shrinking a shrinkable member, and is preferably a heat-shrinkable tube.

The capillary column ends can be most densely and cylindrically bundled by passing the one ends of the plurality of capillary columns through the sleeve formed by a shrinkable member and thereafter shrinking the sleeve. When previously applying the filler to the capillary column surfaces on positions corresponding to the shrinkable member, the clearances between the capillary columns can be filled up with the filler without failure in the process of bundling the capillary columns. When employing a heat-shrinkable tube as the sleeve, the capillary column ends can be bundled by simply heating the same with a dryer or the like.

A mounting member for mounting the sleeve on the polymer charger in an airtight manner is preferably mounted on the sleeve.

The capillary column ends cylindrically bundled by the sleeve can be handled similarly to, for example, a pipe of a liquid chromatograph. For example, if a mounting member such as a ferrule, is mounted on the sleeve when charging the capillary columns with the polymers, the capillary column ends can be fixed to the polymer charger in an airtight manner.

It is preferable that a part to be detected in which the capillary columns are aligned with each other is provided on the side of the cylindrically bundled ends while the capillary columns are two-dimensionally arranged to define a sample injection part on the side of the other ends.

It is possible to dip the capillary column ends in various sample solutions respectively in sample injection for simultaneously injecting samples into the respective capillary columns by two-dimensionally arranging the capillary column ends opposite from the cylindrically bundled ends. Thus, the capillary columns can be reliably charged with the polymers in an exceptional yield. Furthermore, it is possible to apply a electrophoresis voltage across all capillary columns after sample injection for simultaneously separating and detecting the samples in the respective capillary columns.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a side sectional view schematically showing another embodiment;

FIG. 8C is a schematic sectional view taken along the line C–C' in FIG. 8A, while FIG. 8A is taken along the lines A–A' in FIGS. 8B and 8C;

FIGS. 9A to 9C are a schematic top plan view, a schematic front elevational view and a schematic right side sectional view showing a movable plate in the detection side holder fixing part respectively;

FIG. 11 is a model diagram showing a procedure of bundling capillary column ends with a heat-shrinkable tube;

DESCRIPTION OF THE PREFERRED EMBODIMENTS

Figure 1:
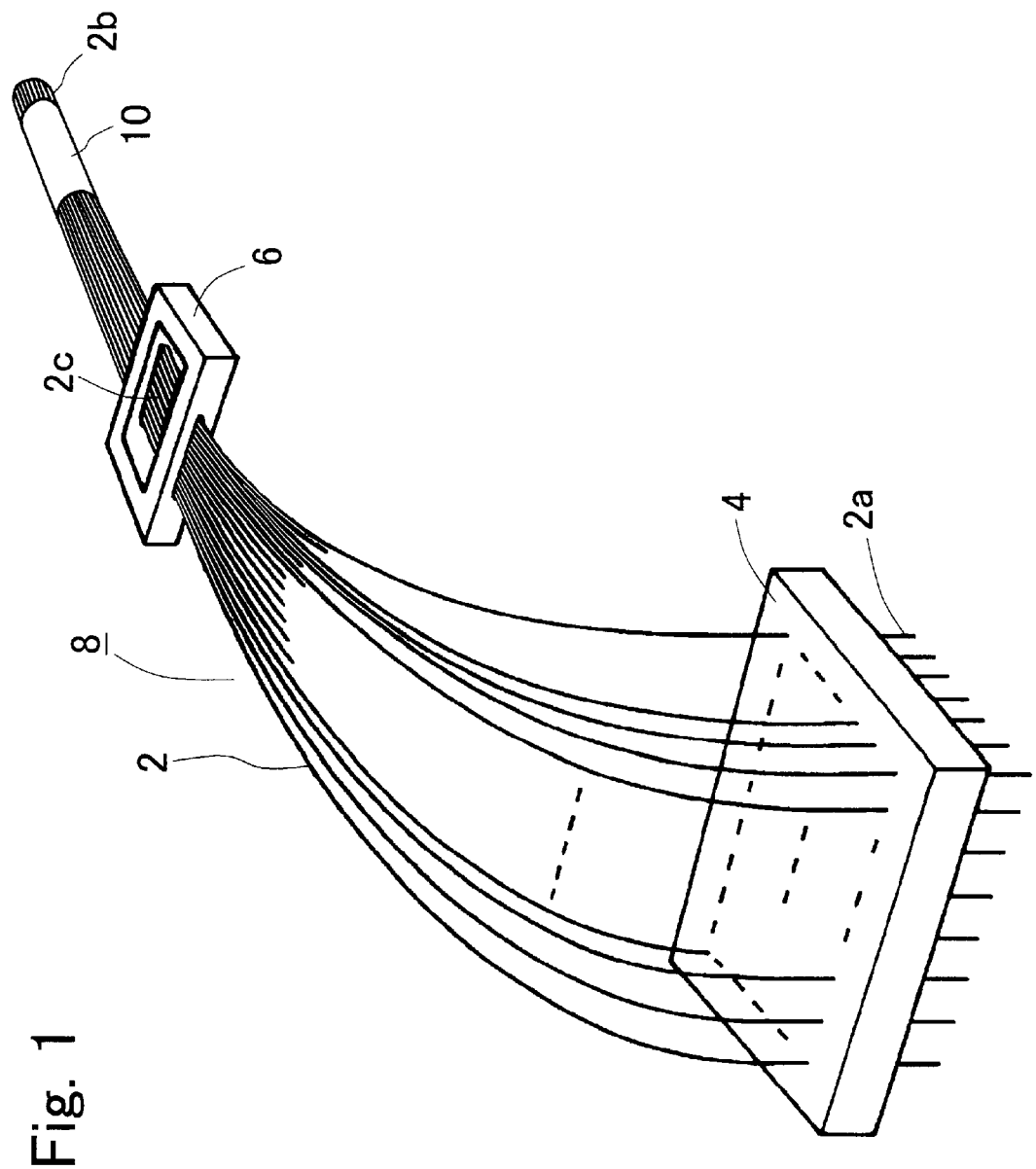
FIG. 1 is a schematic perspective view showing one embodiment applying the present invention to a multi-capillary electrophoretic apparatus.
Figure 2:
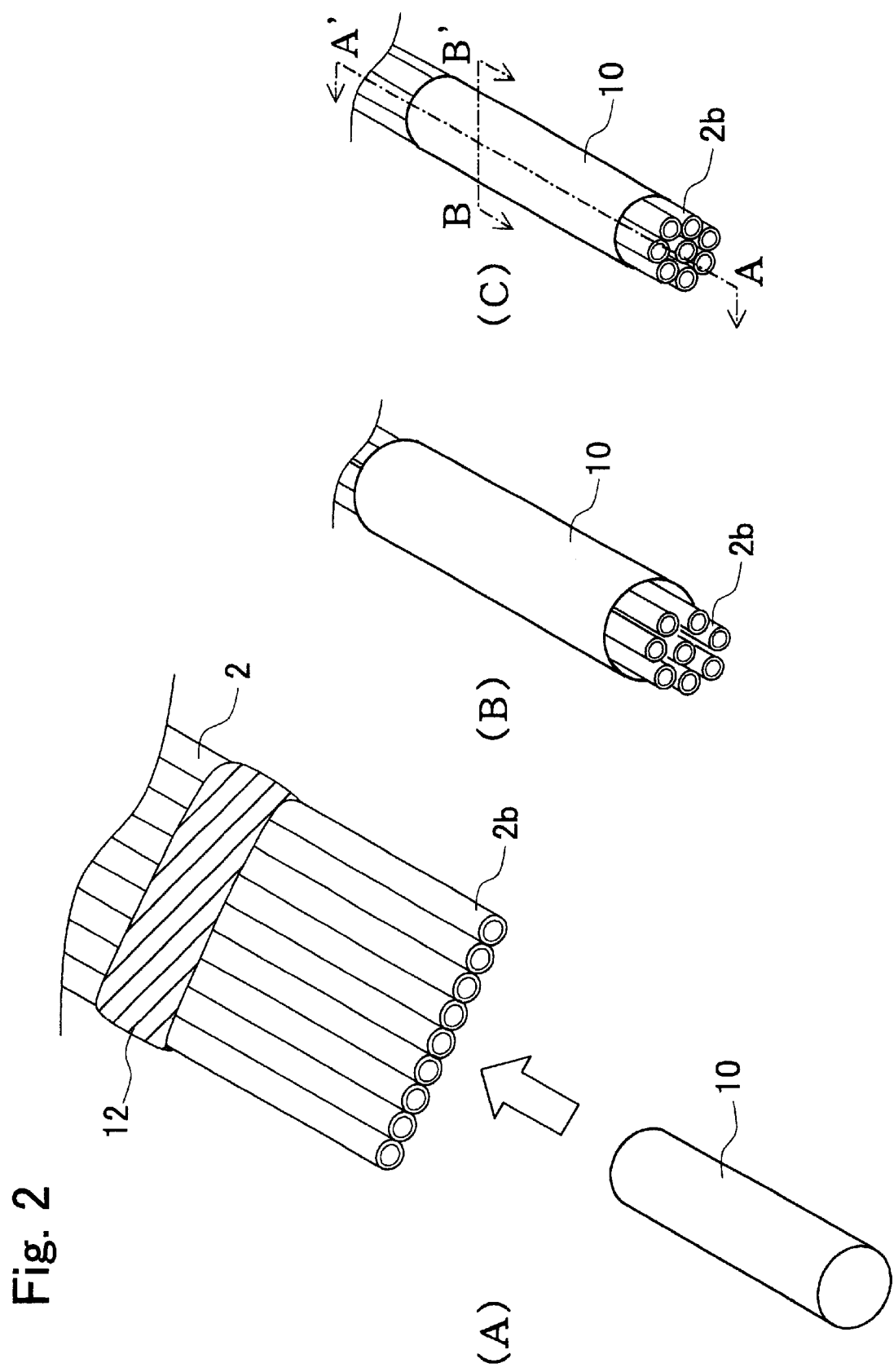
FIG. 2 is a conceptual diagram showing one embodiment of detection means of the embodiment.

FIG. 1 is a schematic perspective view showing one embodiment applying the first aspect of the present invention to a multi-capillary electrophoretic apparatus, which comprises detection means exciting a fluorochrome bonded to a sample component as a label for making the same fluoresce and detecting the fluorescence without influence by Raman scattering or Rayleigh scattering. FIG. 2 is a conceptual diagram showing one embodiment of the detection means of this embodiment This figure shows application to a four-color label DNA sequencer.

A pair of reservoirs 110 and 120 store electrophoresis buffer solutions 112 and 122 respectively, while electrodes 130 and 132 are provided in the buffer solutions 112 and 122 respectively.

Respective wells 102 of a sample plate 100 store samples bonded with fluorochromes having different fluorescent wavelengths such as a fluorescein derivative and a Rhodamine derivative in correspondence to the four types of end bases of DNA fragments. The sample plate 100 is formed with a wiring pattern, in which electrodes are arranged in the wells 102 respectively and connected to a high-voltage wiring cable through a connector part 106 respectively.

A high-voltage switching part 136 switchably connects the reservoir 110 and the sample plate 100 so that wiring can be switched, and an electrophoretic high-voltage power source 134 is connected between the high-voltage switching part 136 and the electrode 132 provided in the other reservoir 120 for switching and applying voltages for sample injection and electrophoresis.

In sample injection, one ends 2a of capillary columns forming a capillary array 2 are inserted one by one into the wells 102 of the sample plate 100, and after the sample injection, the ends 2a are switched to the reservoir 110 to be dipped in the buffer solution 112. The other ends 2b of the capillary columns are dipped in the buffer solution 122 of the other reservoir 120. The second ends 2b are provided with a part to be detected 2c irradiated with excitation light from an optical measuring part 210 detecting the samples by fluorescence so that the fluorescence is measured.

The capillary column ends 2a of the capillary array 2 have two-dimensional arrangement corresponding to the arrangement of the wells 102 of the sample plate 100, while the capillary columns are aligned with each other on the part to be detected 2c and irradiated with the excitation light from a direction perpendicular to the plane of the arrangement of the capillary columns.

A moving mechanism (not shown in FIG. 1) switches and arranges the sample plate 100 and the reservoir 110 as indicated by the broad arrow so that either one selectively comes into contact with the first ends 2a of the capillary columns.

The optical measuring part 210 comprises, for example, a laser beam source 212 such as a mode-locked titanium sapphire laser unit having a repetition rate of 78 MHz, a pulse width of 120 to 150 fs, an oscillation wavelength of 700 to 900 nm and an average output of about 1 W. The energy of one photon of its laser beam is smaller than excitation energy for the fluorochromes.

A dichroic mirror 214 reflecting laser beam is provided on the optical path of the laser beam from the laser beam source 212, so that the laser beam is reflected by the mirror 214 and applied to the part to be detected 2c of the capillary array 2 through a lens 216.

Light from the part to be detected 2c is transmitted to the dichroic mirror 214 through the lens 216. Fluorescence included in the light is transmitted through the dichroic mirror 214 and thereafter separated into prescribed wavelength regions by dichroic mirrors 218, 222 and 226. The dichroic mirror 214 transmits light having a shorter wavelength than the laser wavelength of the excitation light in the light from the lens 216. The light transmitted through the dichroic mirror 214 is transmitted to the dichroic mirror 218 so that light having a wavelength of not more than 510 nm is transmitted through the dichroic mirror 18 and incident upon and detected by a photomultiplier tube (PMT) 220, while light having a wavelength longer than 510 nm is reflected by the dichroic mirror 218 and transmitted to the dichroic mirror 222. In the light from the dichroic mirror 218, light having a wavelength of not more than 560 nm is reflected by the dichroic mirror 222 and incident upon and detected by a photomultiplier tube 224, while light having a wavelength longer than 560 nm is transmitted through the dichroic mirror 222 and transmitted to the dichroic mirror 226. In the light transmitted through the dichroic mirror 222, light having a wavelength of not more than 580 nm is reflected by the dichroic mirror 226 and incident upon and detected by a photomultiplier tube 228, while light having a wavelength longer than 580 nm is transmitted through the dichroic mirror 226 and incident upon and detected by a photomultiplier tube 230.

The optical measuring part 210 is scanned so that the excitation light reciprocates horizontally across the plane of arrangement of the capillary columns on the part to be detected 2c for successively detecting all capillary columns. However, illustration of a scanning mechanism is omitted.

Operations of this embodiment shall now be described with reference to FIGS. 1 and 2.

In sample injection, the one ends 2a of the capillary columns are dipped one by one in the wells 102, while the other ends 2b of the capillary columns are collectively dipped in the buffer solution 122 of the reservoir 120. The high-voltage switching part 136 is connected to the sample plate 100, and the electrophoretic high-voltage power source 134 applies a high voltage between the wells 102 and the reservoir 120. The samples in the wells 102 are injected into the capillary columns.

After the sample injection, application of the high voltage is temporarily stopped and the moving mechanism moves the sample plate 100 and the reservoir 110, thereby dipping the one ends 2a of the capillary columns on a sample side into the buffer solution 112 of the reservoir 110. Thereafter a high voltage is applied between the reservoirs 110 and 120 for performing electrophoretic separation. The voltage for sample injection into the capillary columns and a electrophoresis power supply voltage are, for example, 30 kV and a current capacity is 10 to 30 mA.

Separated sample components successively pass through the part to be detected 2c, and are detected by the optical measuring part 210 at this time.

The laser beam from the laser beam source 212 is applied to the part to be detected 2c through the dichroic mirror 214 and the lens 216 so that the fluorochromes bonded to the samples absorb multiphotons and are excited to fluoresce. The optical measuring part 210 captures the fluorescence so that the photomultiplier tubes 220, 224 and 228 detect fluorescence having a wavelength of not more than 510 nm, fluorescence having a wavelength longer than 510 nm and not more than 560 nm, fluorescence having a wavelength longer than 560 nm and not more than 580 nm and fluorescence having a wavelength longer than 580 respectively.

Base sequence can be determined by bonding the fluorescence having a wavelength of not more than 510 nm, the fluorescence having a wavelength longer than 510 nm and not more than 560 nm, fluorescence having a wavelength longer than 560 nm and not more than 580 nm and the fluorescence having a wavelength longer than 580 to DNA fragment samples for the respective bases respectively.

Since a Raman scattering line generated in the part to be detected 2c due to irradiation with the laser beam has a wavelength at least 700 nm, it does not form background noise in fluorescence detection. Furthermore, the intensity of Rayleigh scattering is advantageously smaller than that of a conventional argon laser beam. In addition, four types of fluorochromes can be efficiently excited with a single laser wavelength due to the multiphoton absorption method, whereby it is not necessary to introduce a plurality of fluorochromes into the same molecule.

The optical measuring part 210 is not restricted to this embodiment but may have any system so far as the same can excite fluorochromes bonded to samples by multiphoton absorption for making the same fluoresce and detect the fluorescence.

While the present invention is applied to a multi-capillary electrophoretic apparatus in this embodiment, the present invention is also applicable to electrophoresis employing a single capillary column.

FIG. 3 is a side sectional view schematically showing one embodiment applying the second aspect of the present invention to a multi-capillary electrophoretic apparatus, and its multi-capillary array-electrophoresis part comprises a detection side holder fixing part fixing a detection side holder and a parallelism adjusting mechanism adjusting the parallelism between a detection part and a part to be detected.

A capillary array 2 is formed by arranging a plurality of capillary columns charged with gels of separation media. One ends (lower ends) 2a of the capillary columns defining a sample injection side are two-dimensionally arranged and fixed by a sample injection side holder 4 to come into contact with a sample in a sample injection reservoir or a buffer solution in a lower reservoir for electrophoresis. The other ends 2b of the capillary columns forming the capillary array 2 define a detection side on which the capillary columns are aligned with each other by a detection side holder 6, and comes into contact with an upper reservoir buffer solution. A part to be detected 2c is provided on the detection side (2b side) of the capillary array on a position where the capillary columns are aligned with each other and supported by the detection side holder 6.

Figure 4:
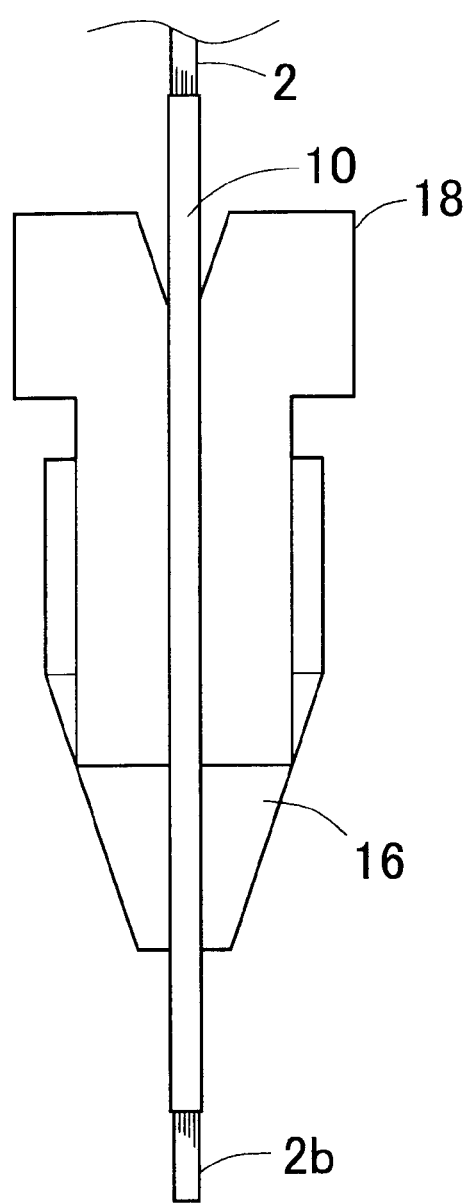
FIG. 4 is a front sectional view showing an exemplary capillary array mounted on the embodiment.
Figure 5:
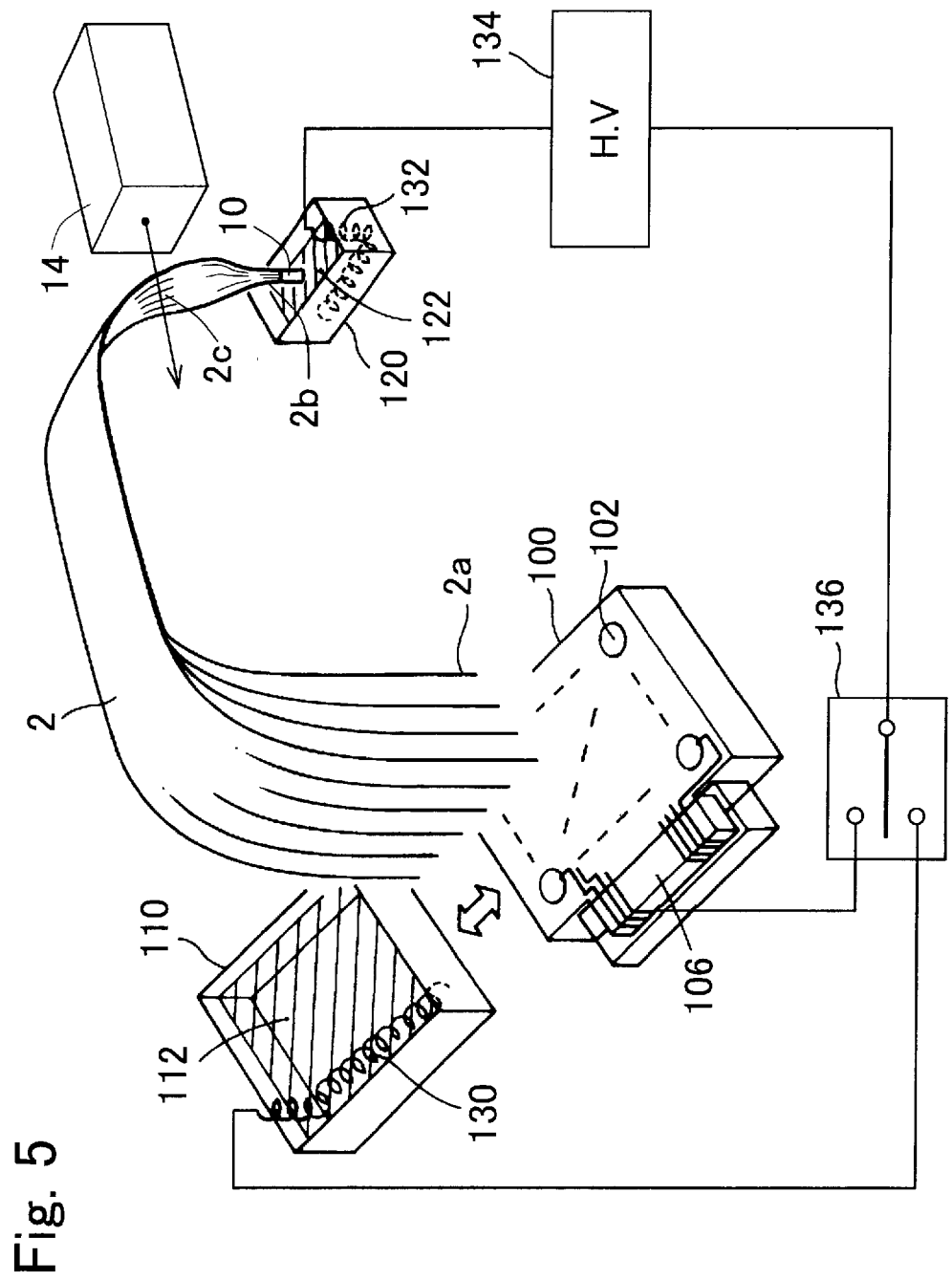
FIG. 5 is a left side elevational view of the capillary array.
Figure 6:
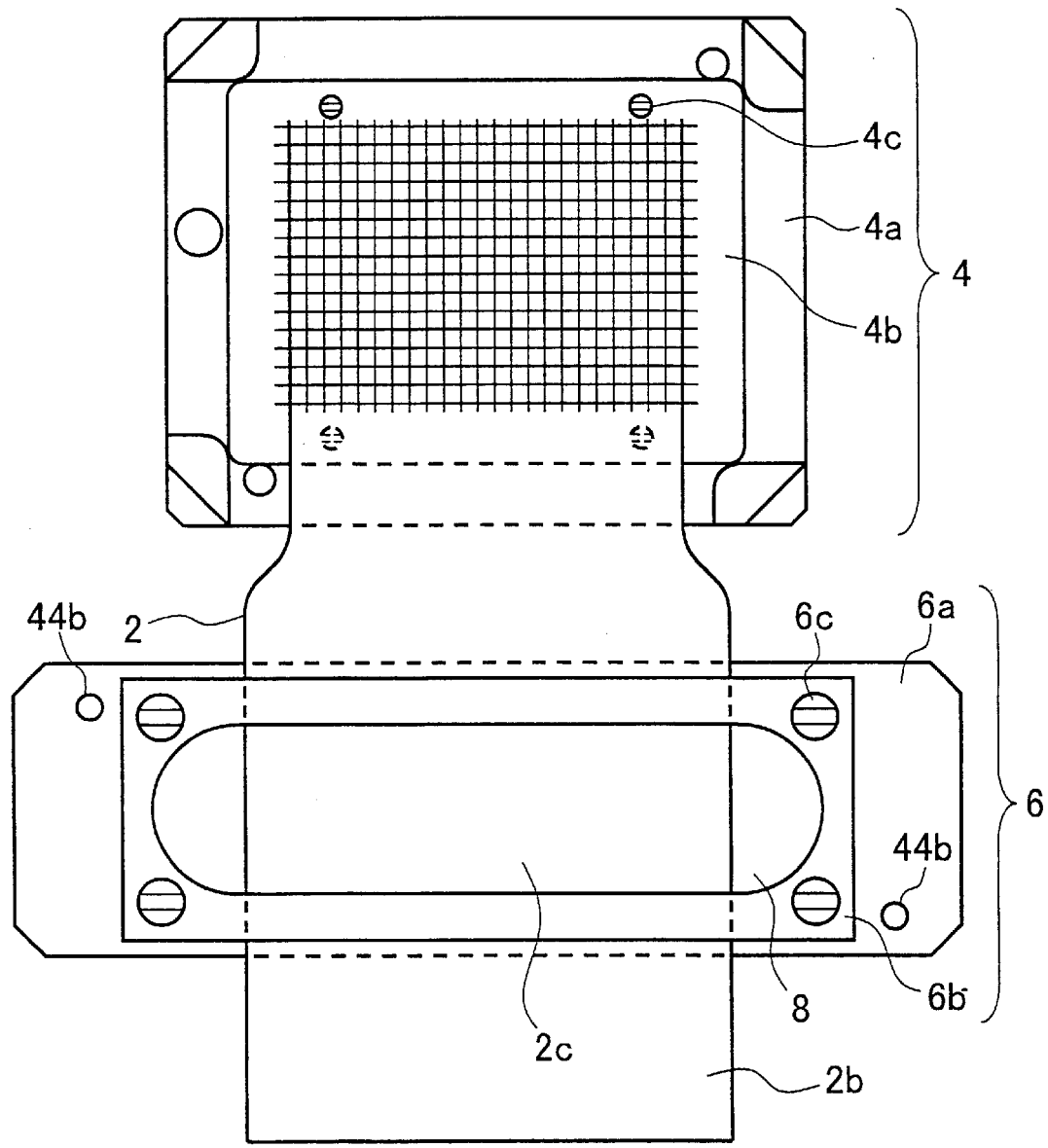
FIG. 6 is a top plan view of the capillary array.

FIGS. 4, 5 and 6 are a schematic front elevational view, a schematic left side elevational view, and a schematic top plan view showing an exemplary capillary array mounted on this embodiment In the sample injection side holder 4, a rubber plate 4d of silicone rubber holding and fixing glass capillary columns in/to holes is held between resin holder plates 4a and 4b for two-dimensionally arranging the capillary columns and integrated by fixed screws 4c. The holder plates 4a and 4b are provided with holes for receiving the capillary columns on 16 by 24 portions in correspondence to the positions of holes of a 384-hole microplate used for sample introduction. The diameters of the holes of the holder plates 4a and 4b are set larger than the outer diameters of the capillary columns. The capillary columns passing through the holder plates 4a and 4b and the rubber plate 4d held therebetween are held in the holes of the rubber plate 4d by elasticity of rubber, to be airtightly fixed to the holder 4.

The detection side holder 6 holds the capillary columns closely arranged on a plane by a holder plate 6a from below and by a rubber plate 6d of silicone rubber from above. In order to press and fix the capillary columns against and to the holder plate 6a with the rubber plate 6d, holder plate 6b is provided for fixing the rubber plate 6d to the holder plate 6a on both side portions of the arrangement of the capillary columns. Fixed screws 6c fix the holder plates 6a and 6b to each other.

The total length of each capillary column is about 500 nm, and the part to be detected 2c is provided on a position of about 400 nm from the end of the sample injection side. In order to form a detection window on the part to be detected 2c, the holder plates 6a and 6b and the rubber plate 6d are provided with elliptic openings 8 extending in the direction of the arrangement of the capillary columns so that the openings 8 overlap with each other on the part to be detected 2c. Signal detection in electrophoresis is performed through the openings 8.

The multi-capillary electrophoretic apparatus according to the present invention is provided on the detection part with location pins 44a guiding the holder 6 to a fixed position as described later, and the holder 6 is provided with location holes 44b receiving the location pins 44a.

Each capillary column is made of quartz glass or borosilicate glass, and has an outer diameter of 200 to 300 $\mu$m and an inner diameter of 75 to 100 $\mu$m. The outer periphery of the capillary column is preferably covered with a film of a non-fluorescent material such as $SiO_2$ not fluorescing or fluorescing to an extent not hindering fluorescence measurement with excitation light of ultraviolet to near infrared regions. In this case, the film may not be removed on the part to be detected 2c. If the capillary column has a fluorescing resin film, the film is removed on the part to be detected 2c.

The capillary columns are charged with a polyacrylamide gel, a linear acrylamide gel, a polyethylene oxide (PEO) gel and the like as gels of separation media. Samples containing four types of DNA fragments labeled with four types of fluorescent materials selected from FAM, JOE, TAMRA, ROX, R6G, R-110 and the like varied with the end bases are injected into the capillary columns respectively and simultaneously electrophoresed.

Referring again to FIG. 3, an argon gas laser unit 10 is provided as an excitation light source for exciting the labeling fluorescent materials. The argon gas laser unit 10 is a multi-line type unit having an output of 40 to 100 mW and simultaneously oscillates laser beams having wavelengths of 488 nm, 514.5 nm and the like.

When applying the multi-capillary electrophoretic apparatus shown in FIG. 3 to an apparatus utilizing multiphoton absorption of the first aspect, a mode-locked titanium sapphire laser unit generating a laser beam having a longer wavelength than fluorescence generated by a labeled fluorochrome is used as the excitation light source in place of the argon gas laser unit 10. The energy of one photon of the laser beam is smaller excitation energy for the fluorochrome.

Figure 7A:
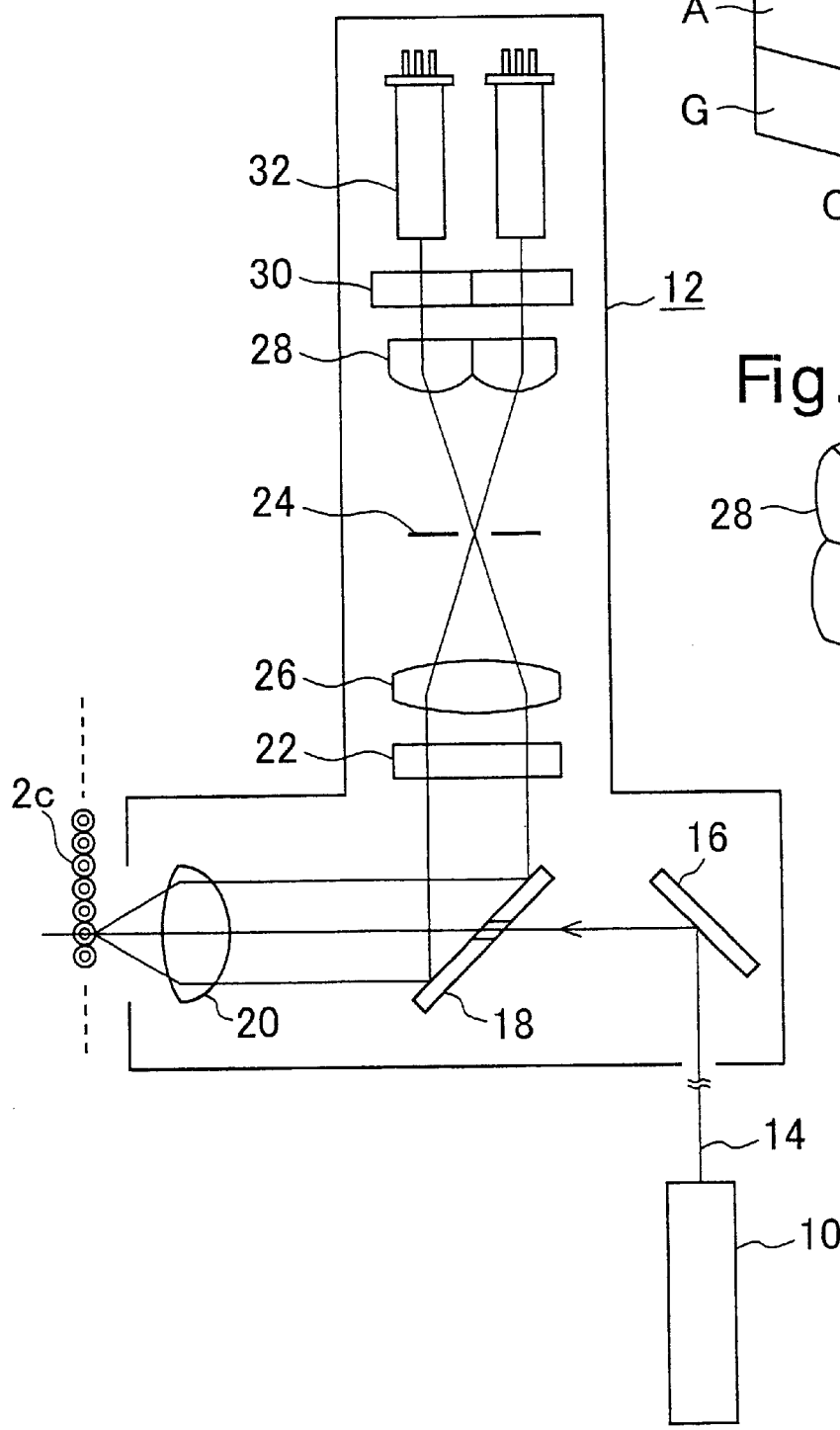
FIG. 7A is a schematic side sectional view showing an optical system in the embodiment.

An optical system 12 applying the laser beam from the laser unit 10 to the part to be detected 2c of the capillary array 2 as excitation light and detecting fluorescence from the part to be detected 2c is an epi-optical system shown in FIG. 7A in detail. Numeral 16 denotes a mirror perpendicularly applying a laser beam 14 from the laser unit 10 to a surface of the part to be detected 2c of the capillary array 2, numeral 18 denotes a tunnel mirror having a hole on its center for transmitting the excitation light beam through the hole and reflecting the fluorescence on a mirror surface, and numeral 20 denotes an objective lens consisting of a condenser lens condensing and projecting the excitation light onto a single capillary column and receiving fluorescence generated from a sample migrating in the capillary column. The objective lens 20 projects the excitation light and receives the fluorescence by the same lens, and forms the epi-optical system. The mirror surface of the tunnel mirror 18 reflects the fluorescence collected by the objective lens 20.

Numeral 22 denotes an optical filter blocking an excitation light component from the reflected light and transmitting the fluorescence, numeral 24 denotes a pinhole slit for limiting a detection field, and numeral 26 denotes a diaphragm lens imaging the fluorescence transmitted through the optical filter 22 on the position of the pinhole slit 24. A fluorescing point in the capillary column is imaged on the position of the pinhole slit 24, thereby forming a confocal optical system. An edge filter or colored glass can be employed as the optical filter 22 for removing the excitation light. The pinhole slit 24 reduces the detection field for preventing invasion of stray light from adjacent capillary columns.

Figure 7C:
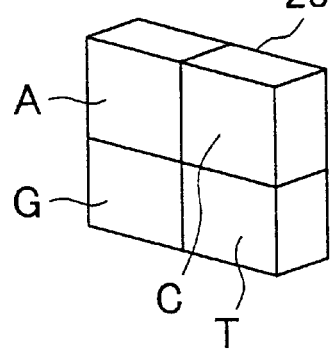
FIG. 7C is a schematic perspective view showing a filter panel employed in FIG. 7A.
Figure 7B:
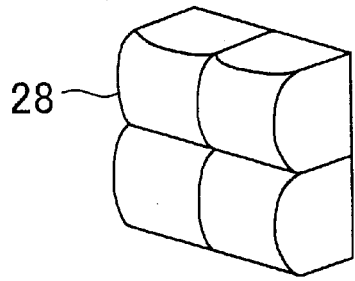
FIG. 7B is a schematic perspective view showing a lens panel employed in FIG. 7A.

In order to divide the fluorescent image on the pinhole slit 24 into four luminous fluxes, a lens panel 28 shown in FIG. 7B is arranged. The lens panel 28 can be manufactured as that prepared by cutting single lenses and sticking the same to each other or a glass molding. A filter panel 30 formed by different spectroscopic filters for respective labeling fluorescent materials shown in FIG. 7C is arranged on optical paths of the four luminous fluxes. The filter panel 30 is a bandpass filter, which is formed by arranging four types of filters having different wavelength characteristics corresponding to the labeling fluorescent materials on the respective optical paths in parallel with each other. The transmission wavelengths of the respective filters correspond to light emission wavelengths of the fluorescent materials labeling fragment samples whose end bases are A (adenine), G (guanine), C (cytosine) and T (thymine). Four photomultiplier tubes 32 are arranged on the respective optical paths for detecting fluorescence transmitted through the filters.

The epi-optical system 12 including the mirror 16, the tunnel mirror 18, the objective lens 20, the optical filter 22, the pinhole slit 24, the diaphragm lens 26, the lens panel 28, the filter panel 30 and the photomultiplier tubes 32 is mounted on a stage of a scanning mechanism 34, and reciprocally moved along a straight line (perpendicular to the plane in FIG. 3 and vertical in FIG. 7A) parallel to the plane of the part to be detected 2c of the capillary array 2 and perpendicular to the electrophoresis direction, in order to detect fluorescence from all capillary columns on the part to be detected 2c. The laser beam 14 is incident upon the mirror 16 in parallel with a scanning direction of the epi-optical system 12, so that the optical axis of the laser beam 14 is not fluctuated by scanning of the epi-optical system 12.

Figure 8A:
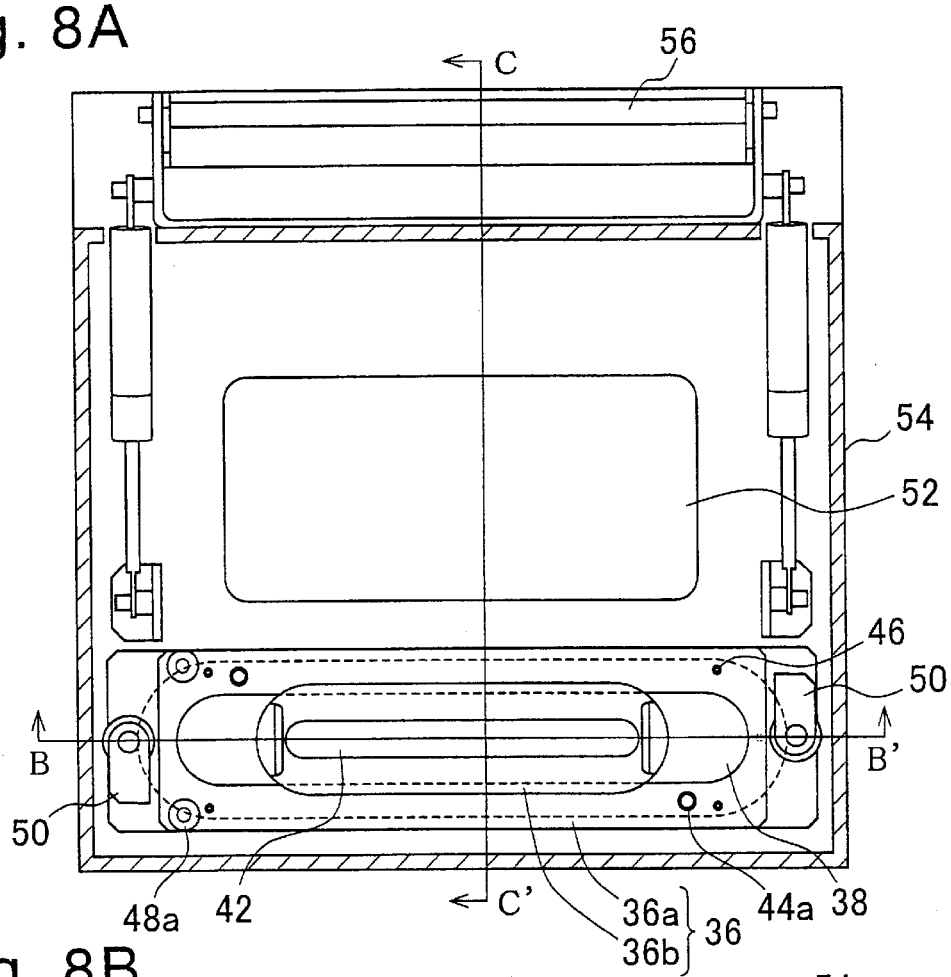
FIG. 8A is a schematic sectional view of one embodiment of a detection side holder fixing part and its periphery in the embodiment as viewed from above.
Figure 8B:
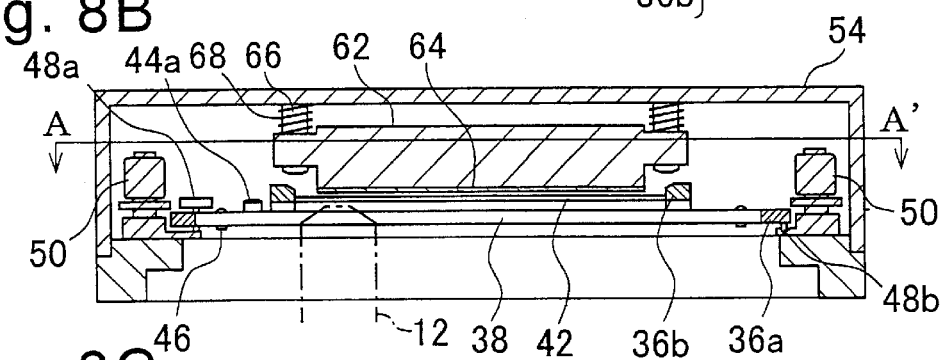
FIG. 8B is a schematic sectional view taken along the line B–B' in FIG. 8A
Figure 8C:
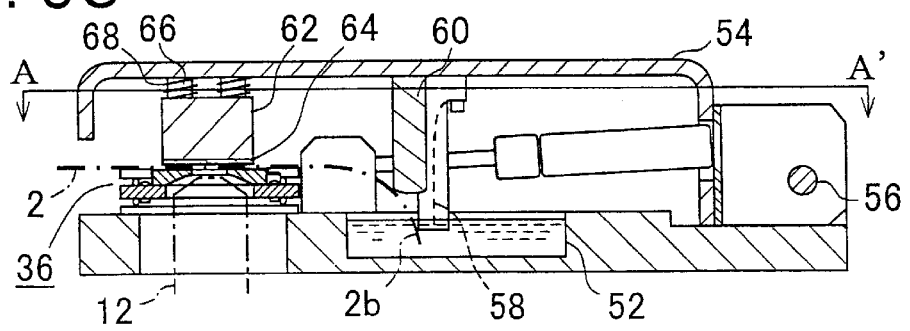

FIG. 8A is a sectional view of one embodiment of the detection side holder fixing part and its periphery as viewed from above, FIG. 8B is a front sectional view taken along the line B–B' in FIG. 8A and FIG. 8C is a side sectional view taken along the line C–C' in FIG. 8A, while FIG. 8A is taken along the lines A–A' in FIGS. 8B and 8C. FIGS. 8A and 8B omit illustration of an upper electrode 58 and a detection side capillary end pressing member 60, and FIG. 8A also omits illustration of a detected part pressing member 62.

A movable plate 36 is provided on a position for fixing the detection side holder 6. FIGS. 9A, 9B and 9C are a top plan view, a front sectional view and a right side elevational view showing the movable plate 36 respectively.

The movable plate 36 is formed by a substrate 36a and a detection position plate 36b. The substrate 36a is provided with a slot 38 in a direction where the epi-optical system 12 is scanned. The detection position plate 36b slightly smaller in dimension than the opening 8 of the detection side holder 6 is arranged on the slot 38. An epi-optical system scanning groove 40 is formed in the detection position plate 36b on the substrate 36a side, and a slot defining a light application window 42 is formed on the bottom surface of the scanning groove 40. The objective lens 20 side of the epi-optical system 12 is arranged in the slot 38 and the scanning groove 40 and scanned along the slot 38.

Two location pins 44a are arranged on positions of the substrate 36a corresponding to the location holes 44b of the holder 6. The holder 6 is correctly arranged on the movable plate 36 by registering the positions of the location pins 44a and the location holes 44b and those of the detection position plate 36b and the opening 8 of the holder 6.

Furthermore, set screws 46 are arranged on the substrate 36a on positions corresponding to four corners of the holder 6. The height for arranging the holder 6 can be adjusted by rotating the set screws 46 and adjusting the length of the set screws 46 projecting from the substrate 36a.

Furthermore, the substrate 36a is provided with a gate angle adjusting mechanism formed by two gate adjusting screws 48a passing through the substrate 36a and a gate adjusting supporting point pin 48b provided on a side opposed to the side provided with the gate adjusting screws 48a and opposite to the detection position plate 36b. The parallelism between the movable plate 36 and a scanning axis of the epi-optical system 12 can be adjusted by rotating the gate adjusting screws 48a.

The holder 6 is fixed to the movable plate 36 by fastening two clamps 50 provided in the vicinity of both ends of the movable plate 36.

An upper reservoir 52 storing a buffer solution for dipping the other ends 2b of the capillary columns forming the capillary array 2 and a cover 54 covering upper portions of the movable plate 36 and the upper reservoir 52 are provided in the vicinity of the movable plate 36. The cover 54 can be opened/closed along a cover switching shaft 56.

The upper electrode 58 covered with a cylindrical insulating member is mounted on the cover 54 and comes into contact with the buffer solution of the upper reservoir 52 in the state covered with the cover 54. A capillary array end pressing member 60 is arranged on the cover 54, for bending the other ends 2b of the capillary columns forming the capillary array 2 toward the upper reservoir 52 and dipping the same in the buffer solution.

The cover 54 is provided with the detected part pressing member 62 on a position corresponding to the part to be detected 2c. The pressing member 62 is formed with a plane smaller in dimension than the opening 8 of the holder 6, and a rubber plate 64 of silicone rubber is stuck to this plane. Four rod members 66 provided on the cover 54 mount the pressing member 62 to be slidable in a direction perpendicular to the plane of the part to be detected 2c. Springs 68 are arranged on the rod members 66 between the cover 54 and the pressing member 62 respectively, so that the pressing member 62 presses the part to be detected 2c against the detection position plate 36b with appropriate pressure through the silicone rubber plate 64 when the cover 54 is closed after arranging the holder 6 on the movable plate 36.

The detection side holder fixing part according to the present invention is formed by the movable plate 36, the gate adjusting screws 48a, the gate adjusting supporting point pin 48b, the clamps 50 and the detected part pressing member 62.

As shown in FIG. 3, the detection side holder 6 is fixed in an electrophoresis chamber 66. A lower electrode 68 is mounted on a lower portion of the chamber 66, to come into contact with a buffer solution in a lower reservoir and communicate with the lower ends 2a of the capillary columns forming the capillary array 2 when the buffer solution in a sample injection reservoir or the lower reservoir for electrophoresis is pushed up to a position coming into contact with the lower ends 2a of the capillary columns. A sample injection voltage or an electrophoresis voltage is applied between the buffer solutions in both reservoirs from a high-voltage power source through the electrodes 58 and 68. For example, the power supply voltage is 30 kV and a current capacity is 10 to 30 mA.

The reservoir for electrophoresis and a sample injection reservoir 70 are arranged in a horizontal plane and supported on an X-Z sample stage 72 under the ends 2a of the capillary columns on the sample injection side of the capillary array 2. The X-Z sample stage 72 performs movement in a horizontal direction (X direction: perpendicular to the plane of FIG. 3) for locating either reservoir under the ends 2a and movement in a vertical direction (Z direction: vertical in FIG. 3) for bringing the buffer solution in the reservoir into contact with the ends 2a or separating the former from the latter by a sample stage moving mechanism 74.

A sample titer plate 76 formed with wells corresponding to the arrangement of the ends 2a of the capillary columns is placed on the reservoir 70. Bottoms of the wells pass through the sample titer plate 76, membranes are formed on the bottoms and samples are adsorbed on the membranes of the wells. The buffer solution in the reservoir 70 comes into contact with the membranes, and the sample injection voltage is applied to the ends 2a of the capillary columns from the lower electrode 68 through the buffer solution.

Operations of fixing the detection side holder 6 to the movable plate 36 and adjusting the parallelism between the plane of the part to be detected 2c and the scanning axis of the epi-optical system 12 shall now be described.

The capillary array 2 having the part to be detected 2c charged with a fluorochrome is prepared so that the holder 6 for the capillary array 2 is arranged on the movable plate 36 by opening the cover 54 and registering the positions of the location pins 44a and the location holes 44b and clamped and fixed by the clamps 50. Thus, the part to be detected 2c of the capillary array 2 can be fixed to the apparatus with excellent reproducibility.

The cover 54 is closed so that the pressing member 62 presses the part to be detected 2c against the detection position plate 36b and fixes the same onto the light application window 42 along the plane of the detection position plate 36b while the pressing member 60 dips the ends 2b of the capillary columns of the capillary array 2 in the buffer solution of the upper reservoir 52.

The epi-optical system 12 is scanned and an image formed on the pinhole slit 24 is observed to determine whether or not the distance between the part to be detected 2c and the objective lens 20 is proper. If the distance between the part to be detected 2c and the objective lens 20 is improper, the gate adjusting screws 48a are rotated for adjusting the distance between the part to be detected 2c and the objective lens 20. Thus, requirement for working accuracy in preparation of the detection side holder 6 and formation of the capillary array 2 can be relieved and reduction of detection sensitivity can be suppressed. Furthermore, since the distance between the part to be detected 2c and the epi-optical system 12 can be adjusted, this electrophoretic apparatus is adaptive to various outer diameters of the capillary columns arranged on the capillary array 2. In addition, outer diameter tolerance by manufacturing lot difference of the capillary columns can be allowed.

While this embodiment employs two gate adjusting screws and the gate adjusting supporting point pin as the gate angle adjusting mechanism, the present invention is not restricted to this but a gate angle may be automatically adjusted in correspondence to a detection signal at the time of scanning the epi-optical system by employing an actuator such as a piezoelectric element, for example.

Alternatively, an actuator moving the epi-optical system along the optical axis of applied light may be provided in place of the gate angle adjusting mechanism for automatically adjusting the distance between the part to be detected and the epi-optical system.

Figure 10:
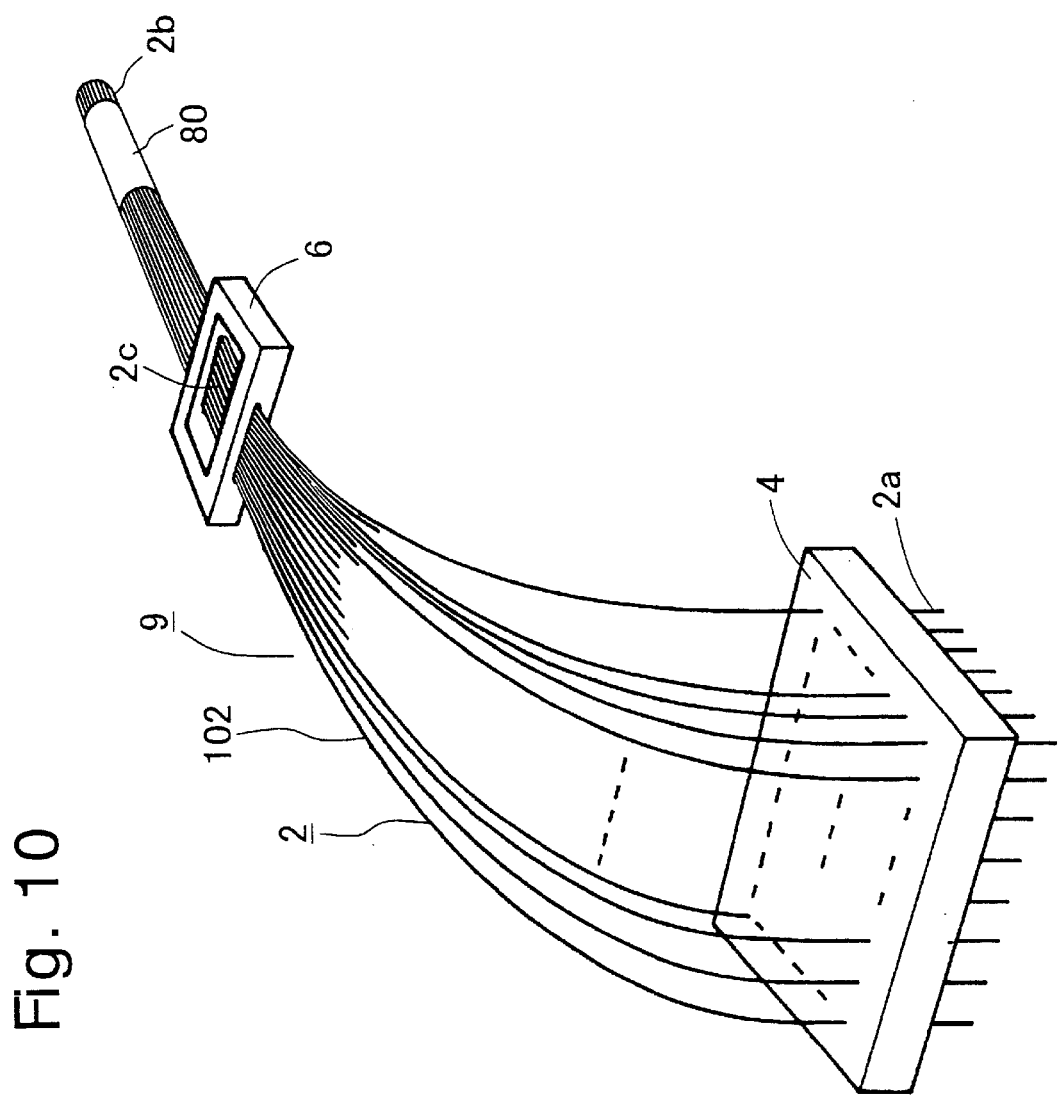
FIG. 10 is a perspective view of a capillary cassette of one embodiment in which a plurality of capillary columns are arranged.

FIG. 10 is a perspective view of a capillary cassette of one embodiment arranging a plurality of capillary columns.

A plurality of capillary columns 102 of a capillary array 2 are arranged, sample injection sides are fixed by a cassette holder 4 and detection sides are fixed by a cassette holder 6 and a heat-shrinkable tube 80 on an end to form a capillary cassette 9. One ends 2a of the capillary columns 102 define a sample injection part and are two-dimensionally arranged and fixed by the cassette holder 4. The other ends 2b of the capillary columns 102 forming the capillary cassette 9 are planarly aligned with each other, fixed by the cassette holder 6, and cylindrically bundled by a shrank heat-shrinkable tube 80. A detection window is formed on the cassette holder 6, and portions of the capillary columns 2 located on the detection window define a part to be detected 2c.

For example, the outer diameter of each capillary column 102 is 300 to 400 µm.

Figure 12A:
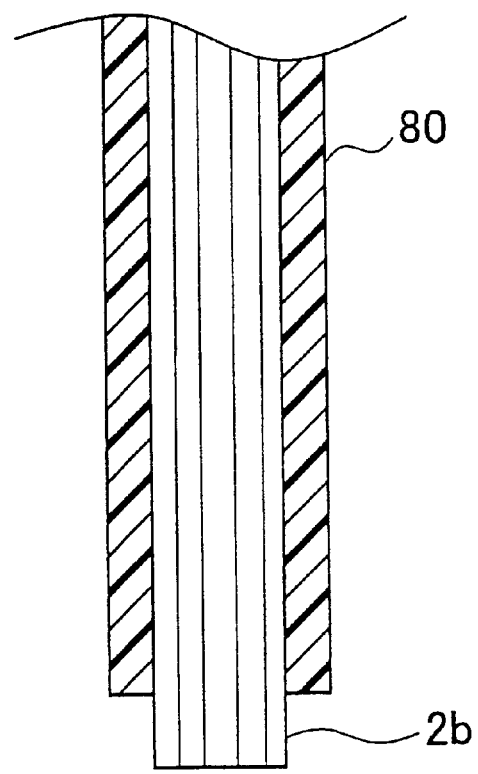
FIGS. 12A and 12B are sectional views taken along the lines A–A' and B–B' showing sections of detection side capillary column ends of the embodiment.
Figure 12B:
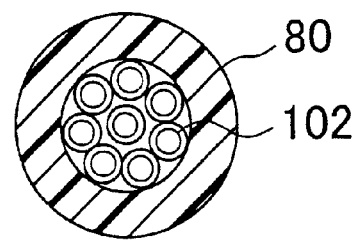

FIGS. 11A to 11C are model diagrams showing a procedure of bundling the ends 2b of the capillary columns 102 by the heat-shrinkable tube 80. FIGS. 12A and 12B are sectional views taken along the lines A–A' and B–B' in FIG. 11C. These figures show the capillary columns 102 in a reduced number.

Manufacturing is performed along the following sequence:

(A) After aligning the plurality of capillary columns 102 with each other, a filler 12 such as an epoxy resin adhesive or a silicon compound is applied to surface portions of the capillary columns 102 on prescribed positions from the ends 2b.

(B) The ends 2b of the capillary columns 102 are bundled and inserted into the heat-shrinkable tube 80, which in turn covers the positions to which the filler 12 is applied.

(C) The heat-shrinkable tube 80 is heated and shrunk. The inner diameter of the heat-shrinkable tube 80 is reduced, the capillary columns 102 adhere to each other, and clearances therebetween are filled up with the filler 12 so that the capillary columns 102 are cylindrically bundled in an airtight manner. Clearances between the heat-shrinkable tube 80 and the capillary columns 102 and between the capillary columns 102 are sealed with the filler 12, and both ends of the heat-shrinkable tube 80 do not communicate with each other except in the capillary columns 102.

Figure 13:
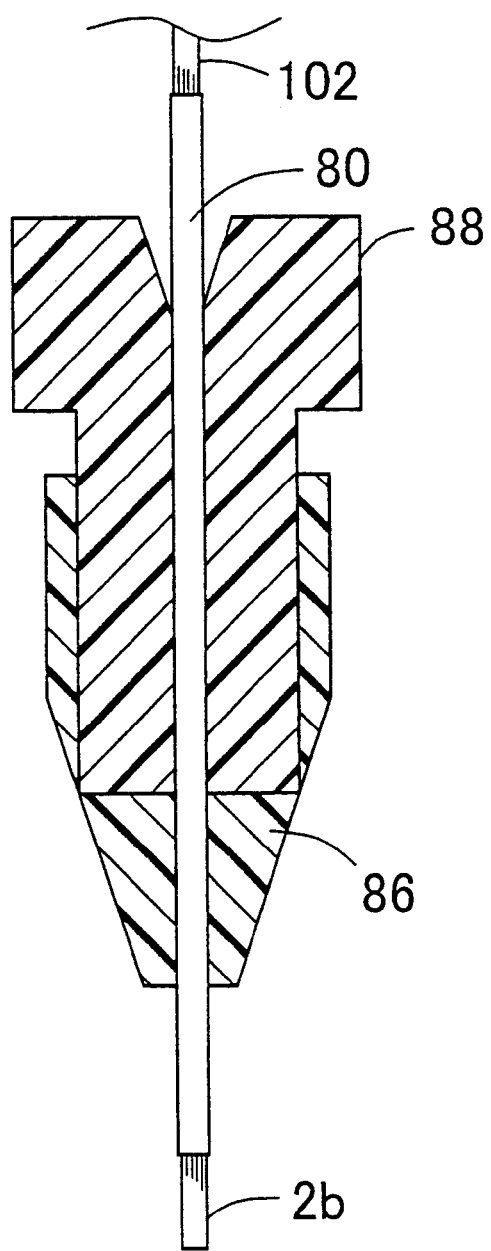
FIG. 13 is a schematic sectional view showing a state of fixing a mounting member for a polymer charger to the capillary column ends.

FIG. 13 is a model diagram showing a method of fixing a mounting member to a polymer charger to the ends 2b of the capillary columns 102.

The capillary columns 102 bundled by the heat-shrinkable tube 80 are inserted into a ferrule 86 serving as the mounting member for the polymer charger along with the heat-shrinkable tube 80 and fixed by a screw 88 so that each capillary column 102 attains sufficient pressure resistance in polymer injection.

It is preferable to set the outer diameter of the shrank heat-shrinkable tube 80 receiving the capillary columns 102 to a pipe outer diameter of a liquid chromatograph such as $\phi1.6$ (outer diameter of 1.6 mm), $\phi2$ or $\phi3$ by adjusting the outer diameters of the capillary columns 102, the number of the capillary columns 102 and the thickness of the shrank heat-shrinkable tube 80. Consequently, an existing ferrule employed for a liquid chromatograph or the like can be employed. When preparing a dedicated ferrule, the capillary columns 102 may be bundled in response to the inner diameter of the dedicated ferrule.

Irregularities of the bundled capillary columns 102 are removed due to the thickness of the heat-shrinkable tube 8, and hence the thickness of the shrunk heat-shrinkable tube 80 is preferably increased.

In polymer charging, the ferrule 86 is connected to and mounted on a connection part of the polymer charger, for charging the capillary columns 2 with polymers by press-filling or suction.

Figure 14:
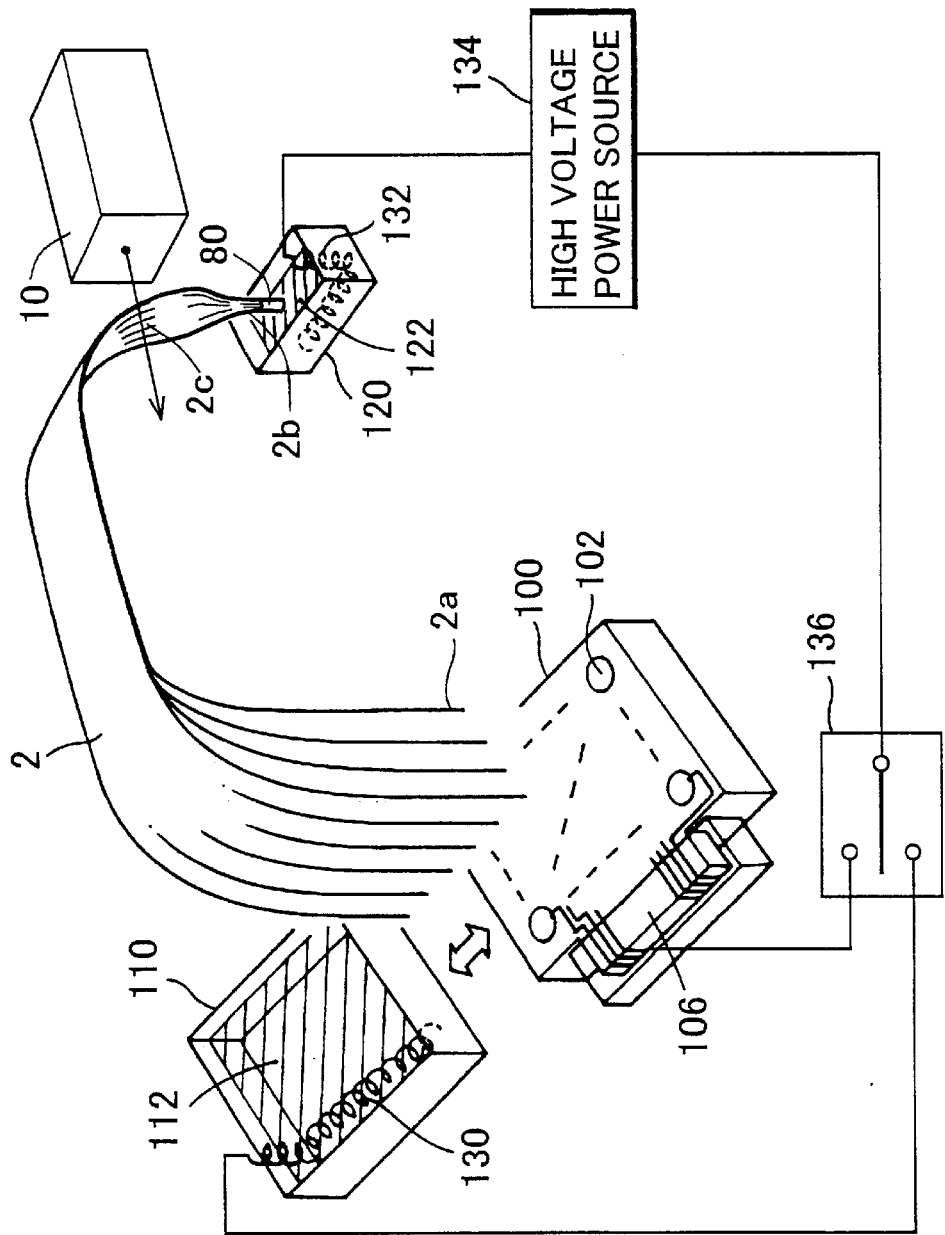
FIG. 14 is a schematic perspective view showing one embodiment of a multi-capillary electrophoretic apparatus to which the embodiment is applied.

FIG. 14 is a schematic perspective view showing one embodiment of a multi-capillary electrophoretic apparatus to which the capillary cassette 9 shown in FIG. 10 is applied. FIG. 14 omits illustration of the cassette holders 4 and 6. This multi-capillary electrophoretic apparatus is identical to that shown in FIG. 1 except the structure on the side of the other ends 2b, and hence redundant description is omitted.

The ends 2b of the capillary columns are bundled by the heat-shrinkable tube 80, and dipped in a buffer solution 122 in a reservoir 120 along with the heat-shrinkable tube 80.

Operations in electrophoretic separation are also identical to those in FIG. 1.

Such a multi-capillary electrophoretic apparatus preferably comprises an automatic polymer charging mechanism for reusing the capillary columns 102 by discharging used polymers from the capillary columns 102 and charging new polymers.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A capillary cassette, comprising:
   a plurality of capillary columns with each capillary column having a first end portion, an opposite second end portion and an intermediate portion disposed between the first and second end portions;
   a boxed-shaped first cassette holder having a pair of opposing surfaces containing a plurality of holes extending therethrough and therebetween with the plurality of holes arranged in a matrix of criss-crossing rows and columns, each hole sized to receive a respective one of the plurality of capillary columns at the first end portion thereof with respective distal ends of the first end portions projecting from one surface of the first cassette holder;
   a tube defining a conduit extending therethrough, the conduit sized to receive and retain the plurality of capillary columns as a bundle at the second end portion thereof; and
   a boxed-shaped second cassette holder having a window formed therethrough, the second cassette holder adapted to receive the plurality of capillary columns at the intermediate portions thereof in a manner that individual ones of the capillary columns are arranged sequentially in a juxtaposed manner for exposure of the individual ones of the capillary columns through the window.

2. A capillary cassette according to claim 1, wherein respective proximal ends of the second end portions of the capillary columns project outwardly from the tube.

3. A capillary cassette according to claim 1, further comprising a resin disposed in the conduit and in contact with and between the tube and the second end portions and in contact with and between contacting ones of the second end portions forming a seal between and among the tube and the second end portions in the conduit.

4. A capillary cassette according to claim 1, further comprising a mounting member having a passageway extending therethrough, the passageway sized to receive and retain the tube therein.

* * * * *

UNITED STATES PATENT AND TRADEMARK OFFICE
CERTIFICATE OF CORRECTION

PATENT NO.        : 6,783,650 B2
APPLICATION NO. : 10/126661
DATED             : August 31, 2004
INVENTOR(S)       : Yoshihide Hayashizaki et al.

It is certified that error appears in the above-identified patent and that said Letters Patent is hereby corrected as shown below:

Title Page item 73
In the Assignee:

The Following Assignee should be added to list:

Japan Science and Technology Corporation, Saitama (JP)

Signed and Sealed this

Fourteenth Day of October, 2008

JON W. DUDAS
*Director of the United States Patent and Trademark Office*